(12) United States Patent
Lee et al.

(10) Patent No.: US 10,787,561 B2
(45) Date of Patent: Sep. 29, 2020

(54) NITRILE RUBBER ARTICLE

(71) Applicant: TOP GLOVE INTERNATIONAL SDN. BHD., Klang, Selangor (MY)

(72) Inventors: May Yin Lee, Selangor (MY); Chong Ban Wong, Selangor (MY)

(73) Assignee: TOP GLOVE INTERNATIONAL SDN. BHD., Klang, Selangor (MY)

( * ) Notice: Subject to any disclaimer, the term of this patent is extended or adjusted under 35 U.S.C. 154(b) by 38 days.

(21) Appl. No.: 16/067,100

(22) PCT Filed: Dec. 27, 2016

(86) PCT No.: PCT/MY2016/050089
§ 371 (c)(1),
(2) Date: Jun. 28, 2018

(87) PCT Pub. No.: WO2017/116227
PCT Pub. Date: Jul. 6, 2017

(65) Prior Publication Data
US 2019/0040238 A1    Feb. 7, 2019

(30) Foreign Application Priority Data
Dec. 30, 2015  (MY) ............... 2015704830

(51) Int. Cl.
| | |
|---|---|
| *C08L 9/04* | (2006.01) |
| *C08J 5/02* | (2006.01) |
| *A61B 42/10* | (2016.01) |
| *C08L 15/00* | (2006.01) |
| *C08L 71/02* | (2006.01) |
| *C08K 3/22* | (2006.01) |

(52) U.S. Cl.
CPC ............. *C08L 9/04* (2013.01); *A61B 42/10* (2016.02); *C08J 5/02* (2013.01); *C08K 3/22* (2013.01); *C08L 15/00* (2013.01); *C08L 71/02* (2013.01); *C08J 2309/04* (2013.01); *C08L 2201/52* (2013.01); *C08L 2312/00* (2013.01)

(58) Field of Classification Search
CPC ........ C08L 9/04; C08L 71/02; C08L 2312/00; C08L 2201/52; C08L 15/00; C08K 3/22; A61B 42/10; C08J 5/02; C08J 2309/04
See application file for complete search history.

(56) References Cited

U.S. PATENT DOCUMENTS

| | | | |
|---|---|---|---|
| 6,989,414 B2 * | 1/2006 | Sata ................. | C08F 218/04 524/375 |
| 2006/0115653 A1 * | 6/2006 | Soerens ............ | A61L 15/225 428/423.1 |
| 2008/0227913 A1 * | 9/2008 | Koide ............... | C08K 3/22 525/54.3 |

FOREIGN PATENT DOCUMENTS

| | | |
|---|---|---|
| WO | 03/006513 A1 | 1/2003 |
| WO | 2007/011309 A1 | 1/2007 |
| WO | 2011/068394 A1 | 6/2011 |
| WO | 2016/072835 A1 | 5/2016 |

OTHER PUBLICATIONS

Dhong, C., et al.; Science Advances, 2019, p. 1-13.*
Buzsard, D.L.; PVC Technology, 1984, Chapter 7, p. 181-213.*

* cited by examiner

*Primary Examiner* — Robert S Jones, Jr.
(74) *Attorney, Agent, or Firm* — Workman Nydegger; Matthew D. Todd

(57) ABSTRACT

A latex formulation for preparing an accelerator-free nitrile rubber article comprising a mixture of at least one base polymer, a crosslinker, and a pH adjuster, wherein the crosslinker is an admixture of metal-based compound, wherein the metal-based compound is a trivalent metal-based compound, polyethylene glycol or derivatives of polyethylene glycol, wherein the polyethylene glycol or derivatives of polyethylene glycol have molecular weight ranging in between 200 Da to 20 000 Da, hydroxide salts, wherein the hydroxide salt is selected from the group consisting of potassium hydroxide, sodium hydroxide, ammonium hydroxide or mixtures thereof, and water, where the latex formulation includes polyethylene oxide, wherein the polyethylene oxide having molecular weight ranging in between 20 kDa to 1000 kDa.

25 Claims, No Drawings

NITRILE RUBBER ARTICLE

FIELD OF THE INVENTION

The present invention relates to a latex formulation and method for preparing the same, in particular a latex formulation for preparing an accelerator-free soft nitrile rubber article with enhanced softness and flexibility and to article produced from said formulation.

BACKGROUND OF THE INVENTION

Natural rubber gloves are widely used as they are capable to protect users hand from various chemicals and pathogens. However, presence of protein in natural rubber (NR) gloves was determined to be the cause of Type I allergy, which was common to glove users. In order to protect the glove users from such allergy, synthetic latexes were introduced. The synthetic latexes are polyisoprene, polychloroprene, polyurethane and acrylonitrile butadiene rubber (NBR). Polyisoprene and polychloroprene gloves showed almost similar properties as the NR gloves but they were not commonly used to produce examination gloves due to high cost of production.

Most of the glove users would opt to use the NBR gloves as they are cost effective than other synthetic latexes. However, elastomeric products made from the acrylonitrile butadiene rubber (NBR) are stiff with very little flexibility as compared to natural rubber and/or other synthetic latexes. The stiffness of the NBR gloves is one of main shortcomings and it is also one of main factors why nitrile surgical gloves are not found widely in the market. It is not suitable to produce nitrile surgical gloves as the gloves have to be thicker and meeting the requirement as to provide protection to both surgeon and patient. As such, there is a need to produce an elastomeric glove that is softer and/or more flexible that is able to provide extra comfort to the end users, in particular a nitrile examination and surgical gloves to overcome the above mentioned shortcoming.

SUMMARY OF THE INVENTION

A latex formulation for preparing an accelerator-free nitrile rubber article comprising a mixture of at least one base polymer, a crosslinker, and a pH adjuster, wherein the crosslinker is an admixture of a) metal-based compound, wherein the metal-based compound is a trivalent metal-based compound, b) polyethylene glycol or derivatives of polyethylene glycol, wherein the polyethylene glycol or derivatives of polyethylene glycol having molecular weight ranging in between 200 Da to 20 000 Da, c) hydroxide salts, wherein the hydroxide salt is selected from the group consisting of potassium hydroxide, sodium hydroxide, ammonium hydroxide or mixtures thereof, and d) water characterized in that the latex formulation includes polyethylene oxide or derivatives of polyethylene oxide, wherein the polyethylene oxide or derivatives of polyethylene oxide having molecular weight ranging in between 20 kDa to 1000 kDa.

An elastomeric glove is produced using latex formulation as described above. The elastomeric glove as claimed in claim 23 having a tensile strength ranging between 14 MPa to 40 MPa, a 500% modulus of 2 MPa to 7.0 MPa and an elongation at break ranging between 500% to 1000%.

Additional aspects, features and advantages of the invention will become apparent to those skilled in the art upon consideration of the following detailed description of preferred embodiments of the invention listed hereinafter.

DETAILED DESCRIPTION OF THE INVENTION

Detailed description of preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claim and for teaching one skilled in the art of the invention. The numerical data or ranges used in the specification are not to be construed as limiting.

The present invention relates to a latex formulation and method for preparing the same, in particular it relates to a latex formulation for preparing an accelerator-free soft nitrile rubber article with enhanced softness and flexibility. The latex formulation prepared in the present invention comprises of at least one base polymer, polyethylene oxide or derivatives of polyethylene oxide, a crosslinker that includes polyethylene glycol or derivatives of polyethylene glycol and a pH adjuster. The polyethylene glycol and the polyethylene oxide minimizes the major setback of the prior art by contributing in the formation of nitrile rubber article with softness maintained before and after aging.

The latex formulation for preparing an accelerator-free soft nitrile rubber article comprises a mixture of at least one base polymer, a crosslinker, a pH adjuster and polyethylene oxide or derivatives of polyethylene oxide. The article prepared using the latex formulation is free of accelerator such as thiurams, thiazole and carbamates. Table 1 shows chemical components used to produce the latex formulation for preparing the accelerator-free soft nitrile rubber article.

TABLE 1

Chemical components used to produce said latex formulation

| Chemicals | Proportion (in parts per hundred rubber, phr) |
|---|---|
| Base Polymer | 100.00 |
| pH Adjuster | 0.80 (based on total dry weight of the base polymer) |
| Crosslinker | 1.20 (based on total dry weight of the base polymer) |
| Polyethylene oxide or derivatives of polyethylene oxide | 0.30 (based on total dry weight of the base polymer) |

The base polymer is selected from synthetic latex, wherein the synthetic latex is selected from the group consisting of carboxylated acrylonitrile, carboxylated polyacrylonitrile butadiene or mixtures thereof, preferably carboxylated polyacrylonitrile butadiene. The carboxylated polyacrylonitrile butadiene is obtained from Shin Foong Chemical Co, which is sold as Polylac 582N. The carboxylated polyacrylonitrile butadiene is a mixture of carboxylated polyacrylonitrile and butadiene. Further, the carboxylated polyacrylonitrile butadiene has 40 to 50% by weight total solid content, while water and surfactants occupying remainder of the mixture.

The pH adjuster used in the latex formulation is selected from either potassium hydroxide or ammonia, preferably ammonia. pH value of the latex formulation is maintained between 9.8 and 10.5. The pH adjuster is used in order to keep the latex produced to be stable. The ammonia is obtained from Kong Long Huat Chemicals Sdn Bhd. In a latex formulation, a base polymer may undergo crosslinking by two ways that is through covalent bonding with sulphur vulcanization (crosslinking via conventional manner) or through ionic bonding with metal ions. In the present invention, the crosslinking materializes by way of ionic bonding.

The crosslinker used in the present invention is an admixture of:
a) metal-based compound;
b) polyethylene glycol or derivatives of polyethylene glycol;
c) hydroxide salts; and
d) water.

The metal-based compound in the crosslinker is selected from either divalent metal-based compound or trivalent metal-based compound, preferably trivalent metal-based compound. The metal-based compound is obtained from Kong Long Huat Chemicals Sdn. Bhd. The trivalent metal-based compound is selected from a group of consisting of chromium (III)-based compound, titanium (III)-based compound, iron (III)-based compound and aluminium-based compound, preferably aluminium-based compound. The chromium (III)-based compound is chromium (III) acetate hydroxide. The titanium (III)-based compound is titanium (III) chloride. The iron (III)-based compound is iron (III) chloride.

The aluminium-based compound is selected from a group of aluminium salts such as aluminium oxide, sodium aluminate, aluminium hydroxide, aluminium stearate, aluminium chloride, aluminium sulphate, aluminium phosphate and mixtures thereof, preferably aluminium hydroxide. Use of the divalent metal-based compound or trivalent metal-based compound in the cross-linker formulation eliminates the need of sulphur, accelerators and common metal oxides (for instance zinc oxide).

The polyethylene glycol or derivatives of polyethylene glycol in the crosslinker is selected from any polyethylene glycol with molecular weight between 200 Da to 20 kDA, preferably polyethylene glycol with molecular weight of 200 Da. The polyethylene glycol or derivatives of polyethylene glycol is obtained from IMCD Malaysia Sdn. Bhd. In the interim, the hydroxide salt in the crosslinker is selected from the group consisting of potassium hydroxide, sodium hydroxide, ammonium hydroxide and mixtures thereof, preferably sodium hydroxide. The hydroxide salt is obtained from Kong Long Huat Chemicals Sdn. Bhd. The hydroxide salt is of concentration between 1 to 10%.

Meanwhile, the polyethylene oxide or derivatives of polyethylene oxide in the latex formulation is selected from any polyethylene oxide or derivatives of polyethylene oxide with molecular weight between 20 kDa to 1000 kDa, preferably polyethylene oxide or derivatives of polyethylene oxide with molecular weight of 600 kDa. The polyethylene oxide is obtained from Dow Company, which is sold as Polyox WSR 205.

A method for preparing said cross-linker formulation is disclosed. The method comprises steps of dissolving metal-based compound in an aqueous hydroxide salt producing a mixture, wherein the aqueous hydroxide salt is of 40% to 60% concentration. The mixture is then stirred for an hour at a temperature ranging between 40° C. to 80° C., preferably at 60° C. until a clear solution is produced. The polyethylene glycol or derivatives of polyethylene glycol is added to the clear solution and stirred for an hour at room temperature to produce the crosslinker. The polyethylene glycol or derivatives of polyethylene glycol is first diluted to a dilution factor ranging from 5% to 20%, preferably 10% before it is added to the clear solution.

The crosslinker formulation contains 1% to 5% by weight, preferably 3% by weight of the metal-based compound. The crosslinker formulation further contains 10% to 30% by weight, preferably 20% by weight of the polyethylene glycol or derivatives of polyethylene glycol. Still further, the crosslinker formulation contains 1% to 10% by weight, preferably 6% by weight of the hydroxide salt. The remaining of the crosslinker contains water.

Third embodiment of the present invention discloses a method for preparing the latex formulation, in particularly preparation of carboxylated polyacrylonitrile butadiene latex formulation. The method comprises the steps of mixing a base polymer with the crosslinker prepared as discussed above to produce a mixture. pH adjuster is added to the mixture producing a new mixture. The new mixture is then stirred for an hour. Optionally, additives can also be added to the new mixture, where the additive is at least one or more additive(s) selected from the group consisting of antiozonants or antioxidants, stabilizers, fillers, pigments or mixtures thereof.

The polyethylene oxide or derivatives of polyethylene oxide is added to the new mixture. Water is then added to a mixture resulting from combination of the new mixture and the polyethylene oxide or derivatives of polyethylene oxide to produce a compounded latex. The water is added in order to attain a total solid content ranging in between 13% to 30% by w/w of intended glove weight. Lastly, the compounded latex is allowed for maturation for 18 hours to 48 hours, preferably 24 hours whilst maintaining pH value of the compounded latex in between 9.8 and 10.5. The compounded latex is carboxylated polyacrylonitrile butadiene (NBR). The compounded latex contains 0.30 phr to 1.50 phr, preferably 0.80 phr of the pH adjuster. The compounded latex also contains 0.50 phr to 1.50 phr, preferably 1.20 phr of the crosslinker. Still further, the compounded latex contains 0.20 phr to 1.00 phr, preferably 0.30 phr of the polyethylene oxide or derivatives of polyethylene oxide.

The accelerator-free soft nitrile rubber article prepared is an elastomeric glove. Method of manufacturing elastomeric glove using latex formulation prepared as disclosed above adopts a method commonly known in the glove manufacturing industry. The method comprises the steps of a) washing formers with acid and alkaline, b) dipping formers obtained from step (a) into a coagulant mixture, wherein the coagulant mixture comprises of calcium nitrate, wetting agent and anti-tacking agent, c) dipping the coagulated formers obtained from step (b) into the compounded latex, as discussed above, d) leaching the latex coated formers obtained from step (c) with warm water that has a temperature between 60° C. to 70° C. to produce glove, e) curing the glove on the formers obtained from step (d) in an oven for a period between 15 minutes to 30 minutes, preferably 20 minutes at a temperature between 70° C. to 160° C., preferably 120° C. to dry the glove on formers, f) chlorinating the glove on the formers obtained from step (e) for donning purposes, and g) drying and stripping the glove, in particular an accelerator-free soft elastomeric glove. Instead of chlorination process in step (f), the gloves obtained from step (d) may be subjected to polymer coating for donning purpose. Apart from that, instead of chlorination process in step (f), the gloves obtained from step (e) are dipped in cornstarch slurry for donning purpose.

The accelerator-free soft elastomeric glove prepared having a thickness ranging between 0.05 mm to 0.15 mm, a tensile strength ranging between 14 MPa to 40 MPa, a 500% modulus of less than 7 MPa, preferably 2 MPa to 6.5 MPa and an elongation at break ranging between 500% to 1000%, preferably between 650% to 850%. The properties mentioned above remains about the same before and after aging. Aging treatment of the elastomeric glove is conducted in an oven as per ASTM standard glove aging method.

The treatment can be executed using either of two following conditions:
  i. heating at a temperature of 100° C. for a period of 22 hours; or
  ii. heating at a temperature of 70° C. for a period of 7 days (or about 168 hours).

The elastomeric product using the above mentioned latex formulation can also be extended for preparing finger cots and any other dipped latex product. The following examples are constructed to illustrate the present invention in a non-limiting sense.

Example 1

Preparation of cross-linker
  i. dissolving aluminium hydroxide in aqueous 40% to 60% concentration of sodium hydroxide solution to produce a mixture;
  ii. stirring the mixture obtained in step (i) at a temperature of 60° C. until a clear solution is obtained; and
  iii. adding polyethylene glycol into the solution obtained from step (ii) to produce the cross-linker, wherein the crosslinker contains 3% by weight of aluminium hydroxide, 6% by weight of sodium hydroxide and 20% by weight of the polyethylene glycol.

Example 2

Preparation of the latex formulation
  i. mixing carboxylated polyacrylonitrile butadiene with the crosslinker obtained from example 1;
  ii. adding ammonia into the mixture obtained in step (i);
  iii. stirring the mixture obtained from step (ii) for a duration of 1 hour;
  iv. adding polyethylene oxide into the mixture obtained from step (iii) to produce carboxylated polyacrylonitrile butadiene (NBR) latex formulation, wherein latex formulation contains 0.8 phr of the ammonia, 1.2 phr of the crosslinker and 0.3 phr of polyethylene oxide or derivatives of polyethylene oxide;
  v. adding water to the latex formulation obtained from step (iv) to achieve a total solid content between 13% to 30% by w/w; and
  vi. allowing resulting mixture obtained from step (v) for maturation for 24 hours,
wherein the pH range of the latex formulation after step (vi) is sustained between 9.8 to 10.5, wherein the crosslinker is an admixture of an aluminium hydroxide, polyethylene glycol, aqueous sodium hydroxide and water, and optionally, adding antiozonants or antioxidants, stabilizers, fillers, pigments or mixtures thereof to the carboxylated polyacrylonitrile butadiene (NBR) latex formulation obtained in step (iv). Table 2 shows the chemical components used in this example to produce said latex formulation.

TABLE 2

Chemical components used to produce said latex formulation

| Chemicals | Parts per hundred rubber (phr) |
| --- | --- |
| Carboxylated polyacrylonitrile butadiene latex | 100.0 |

TABLE 2-continued

Chemical components used to produce said latex formulation

| Chemicals | Parts per hundred rubber (phr) |
| --- | --- |
| Ammonia | 0.8 (based on total dry weight of the base polymer) |
| Crosslinker | 1.2 (based on total dry weight of the base polymer) |
| Polyethylene oxide or derivatives of polyethylene oxide | 0.3 (based on total dry weight of the base polymer) |

Example 3

Manufacturing carboxylated polyacrylonitrile butadiene (NBR) glove using latex formulation as prepared in example 2 adopting method commonly known in the glove manufacturing industry. Mechanical properties (i.e. tensile strength, modulus at 500% and elongation at break) of the prepared NBR glove are tested according to standard ASTM testing method. Tables 3 to 5 show the mechanical properties of the NBR glove prepared using different type of aluminium-based compound. NBR gloves prepared are of 5 grams of examination gloves and 7.5 grams of surgical gloves.

TABLE 3

Tensile strength of the NBR glove using different type of aluminium-based compound

| | Tensile strength (MPa) | |
| --- | --- | --- |
| Type of Aluminium Salt | Before Aging | After Aging |
| Aluminium sulphate | 22.64 | 26.37 |
| Aluminium chloride | 24.95 | 26.72 |
| Aluminium hydroxide | 19.59 | 21.97 |
| Sodium aluminate | 22.47 | 25.83 |

TABLE 4

Elongation at break of the NBR glove using different type of aluminium-based compound

| | Elongation at Break (%) | |
| --- | --- | --- |
| Type of Aluminium Salt | Before Aging | After Aging |
| Aluminium sulphate | 729.6 | 712.9 |
| Aluminium chloride | 704.2 | 691.3 |
| Aluminium hydroxide | 756.1 | 730.8 |
| Sodium aluminate | 716.5 | 705.4 |

TABLE 5

Modulus at 500% (MPa) of the NBR glove using different type of aluminium-based compound

| | Modulus at 500% (MPa) | |
| --- | --- | --- |
| Type of Aluminium Salt | Before Aging | After Aging |
| Aluminium sulphate | 4.447 | 5.034 |
| Aluminium chloride | 5.569 | 5.571 |
| Aluminium hydroxide | 4.281 | 4.911 |
| Sodium aluminate | 4.951 | 5.310 |

Glove produced using latex formulation of the present invention is able to achieve modulus at 500% of less than 6 MPa, resulting in glove with softness maintained before and after aging.

Further, tables 6 to 9 shows mechanical properties (i.e. tensile strength, elongation at break, modulus at 300% and modulus at 500%) of the NBR glove using different type of trivalent metals. Trivalent metals used for preparation of the NBR gloves for this testing are chromium (III) acetate hydroxide, titanium (III) chloride, iron (III) chloride and aluminium hydroxide respectively.

TABLE 6

Tensile strength (MPa) of the NBR glove using different type of trivalent metals

| Type of Trivalent Metals | Tensile strength (MPa) | |
| --- | --- | --- |
| | Before Aging | After Aging |
| Chromium (III) | 19.9 | 19.9 |
| Titanium (III) | 19.0 | 20.2 |
| Iron (III) | 17.5 | 17.6 |
| Aluminium | 23.6 | 26.6 |

TABLE 7

Elongation at Break (%) of the NBR glove using different type of trivalent metals

| Type of Trivalent Metals | Elongation at Break (%) | |
| --- | --- | --- |
| | Before Aging | After Aging |
| Chromium (III) | 759.3 | 796.0 |
| Titanium (III) | 734.9 | 814.4 |
| Iron (III) | 998.4 | 914.1 |
| Aluminium | 837.7 | 822.7 |

TABLE 8

Modulus at 300% (MPa) of the NBR glove using different type of trivalent metals

| Type of Trivalent Metals | Modulus at 300% (MPa) | |
| --- | --- | --- |
| | Before Aging | After Aging |
| Chromium (III) | 2.26 | 2.32 |
| Titanium (III) | 2.32 | 2.26 |
| Iron (III) | 2.05 | 2.02 |
| Aluminium | 2.44 | 2.49 |

TABLE 9

Modulus at 500% (MPa) of the NBR glove using different type of trivalent metals

| Type of Trivalent Metals | Modulus at 500% (MPa) | |
| --- | --- | --- |
| | Before Aging | After Aging |
| Chromium (III) | 3.89 | 3.80 |
| Titanium (III) | 3.98 | 3.95 |
| Iron (III) | 3.30 | 3.34 |
| Aluminium | 4.30 | 4.48 |

Tables 10 to 12 show comparison of mechanical properties of the NBR glove prepared using the present invention and glove prepared using prior art accelerator-free vulcanization system. Crosslinker used for preparation of the NBR glove for this testing is aluminium hydroxide. NBR gloves prepared are of 5 grams of examination gloves and 7.5 grams of surgical gloves.

TABLE 10

Tensile strength (MPa) of the NBR glove of the present invention and prior arts

| Type of Trivalent Metals | Tensile strength (MPa) | |
| --- | --- | --- |
| | Before Aging | After Aging |
| Prior art (Exam Glove) | 30.91 | 31.07 |
| Present invention (Exam Glove) | 22.63 | 25.89 |
| Prior art (Surgical Glove) | 29.36 | 26.57 |
| Present invention (Surgical Glove) | 20.91 | 22.62 |

TABLE 11

Elongation at Break (%) of the NBR glove of the present invention and prior arts

| Type of Trivalent Metals | Elongation at Break (%) | |
| --- | --- | --- |
| | Before Aging | After Aging |
| Prior art (Exam Glove) | 595.0 | 600.8 |
| Present invention (Exam Glove) | 700.6 | 709.9 |
| Prior art (Surgical Glove) | 657.0 | 628.3 |
| Present invention (Surgical Glove) | 788.4 | 745.1 |

TABLE 12

Modulus at 500% (MPa) of the NBR glove of the present invention and prior arts

| Type of Trivalent Metals | Modulus at 500% (MPa) | |
| --- | --- | --- |
| | Before Aging | After Aging |
| Prior art (Exam Glove) | 18.44 | 17.84 |
| Present invention (Exam Glove) | 4.90 | 5.02 |
| Prior art (Surgical Glove) | 14.27 | 15.03 |
| Present invention (Surgical Glove) | 4.36 | 5.56 |

Glove produced using latex formulation of the present invention is able to achieve modulus at 500% of less than 6 MPa that is much lower than glove produced using latex formulation of the prior arts. Based on the result, it is also apparent that glove produced using latex formulation of the present invention achieves enhanced elongation at break than glove produced using latex formulation of the prior arts. As a whole, the elastomeric glove prepared using the present invention gives a better and/or enhanced softness and flexibility as compared to glove prepared using other accelerator-free system and/or or conventional sulfur vulcanization system.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including", and "having" are inclusive and therefore specify the presence of stated to features, integers, steps, operations, elements, and/or components, but do not preclude the presence or addition of one or more other features, integers, steps, operations, elements, components, and/or groups thereof.

The method steps, processes, and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

Wherever a range of values is specified, a value up to 10% below and above the lowest and highest numerical value respectively, of the specified range, is included in the scope of the disclosure. The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The invention claimed is:

1. A latex formulation for preparing an accelerator-free nitrile rubber article comprising a mixture of at least one base polymer, a crosslinker, and a pH adjuster, wherein the crosslinker is an admixture of:
   a) metal-based compound, wherein the metal-based compound is a trivalent metal-based compound;
   b) polyethylene glycol or a derivatives of polyethylene glycol, wherein the polyethylene glycol or derivatives of polyethylene glycol has a molecular weight ranging from 200 Da to 20 000 Da;
   c) a hydroxide salts, wherein the hydroxide salt is selected from the group consisting of potassium hydroxide, sodium hydroxide, ammonium hydroxide and mixtures thereof; and
   d) water, wherein:
      the latex formulation includes polyethylene oxide,
      the polyethylene oxide has a molecular weight ranging from 20 kDa to 1000 kDa,
      the latex formulation contains 0.2 to 1.0 phr (dry weight) of the polyethylene oxide, and
      the latex formulation contains 0.15 to 0.45 phr (dry weight) of the polyethylene glycol or the derivatives of polyethylene glycol from the crosslinker.

2. The latex formulation as claimed in claim 1 wherein the nitrile rubber article is an elastomeric glove.

3. The latex formulation as claimed in claim 1 wherein the base polymer is synthetic latex.

4. The latex formulation as claimed in claim 3 wherein the synthetic latex is selected from the group consisting of carboxylated acrylonitrile, carboxylated polyacrylonitrile butadiene and mixtures thereof.

5. The latex formulation as claimed in claim 3 wherein the synthetic latex is carboxylated polyacrylonitrile butadiene.

6. The latex formulation as claimed in claim 1 wherein the latex formulation contains 0.5 to 1.5 phr (dry weight) of the crosslinker.

7. The latex formulation as claimed in claim 1 wherein the trivalent metal-based compound is aluminium-based compound.

8. The latex formulation as claimed in claim 6 wherein the aluminium-based compound is selected from the group of aluminium salts consisting of aluminium oxide, sodium aluminate, aluminium hydroxide, aluminium stearate, aluminium chloride, aluminium sulphate, aluminium phosphate and mixtures thereof.

9. The latex formulation as claimed in claim 7 wherein the aluminium-based compound is aluminium hydroxide.

10. The latex formulation as claimed in claim 6 wherein the latex formulation contains 0.005 to 0.075 phr (dry weight) of the metal-based compound from the crosslinker.

11. The latex formulation as claimed in claim 6 wherein the latex formulation contains 0.036 phr (dry weight) of the metal-based compound from the crosslinker.

12. The latex formulation as claimed in claim 6 wherein the latex formulation contains 0.24 phr (dry weight) of the polyethylene glycol or the derivatives of polyethylene glycol from the crosslinker.

13. The latex formulation as claimed in claim 1 wherein the hydroxide salt is sodium hydroxide.

14. The latex formulation as claimed in claim 6 wherein the latex formulation contains 0.005 to 0.15 phr (dry weight) of the hydroxide salt from the crosslinker.

15. The latex formulation as claimed in claim 6 wherein the latex formulation contains 0.72 phr (dry weight) of the hydroxide salt from the crosslinker.

16. The latex formulation as claimed in claim 1 wherein the latex formulation contains 0.8 phr (dry weight) of the pH adjuster, the pH adjuster comprising ammonia.

17. The latex formulation as claimed in claim 1 wherein the pH adjuster is selected from either potassium hydroxide or ammonia.

18. The latex formulation as claimed in claim 17 wherein the pH adjuster is ammonia.

19. The latex formulation as claimed in claim 1 wherein the latex formulation contains 0.3 phr (dry weight) of the polyethylene oxide.

20. The latex formulation as claimed in claim 1 wherein the pH adjuster is added to the latex formulation so that pH value of the latex formulation is maintained between 9.8 and 10.5.

21. The latex formulation as claimed in claim 1 wherein the latex formulation further includes at least one additive selected from the group consisting of antiozonants or antioxidants, stabilizers, fillers, pigments or mixtures thereof.

22. An elastomeric glove produced using latex formulation as claimed in claim 1.

23. The elastomeric glove as claimed in claim 22 having a tensile strength ranging between 14 MPa to 40 MPa, a 500% modulus of 2 MPa to 7.0 MPa and an elongation at break ranging between 500% to 1000%.

24. A latex formulation for preparing an accelerator-free nitrile rubber article comprising a mixture of at least one base polymer, a crosslinker, and a pH adjuster, wherein the crosslinker is an admixture of:
   a) metal-based compound, wherein the metal-based compound is a trivalent metal-based compound;
   b) polyethylene glycol or a derivative of polyethylene glycol, wherein the polyethylene glycol or derivative of polyethylene glycol has a molecular weight ranging from 200 Da to 20 000 Da;
   c) a hydroxide salt, wherein the hydroxide salt is selected from the group consisting of potassium hydroxide, sodium hydroxide, ammonium hydroxide and mixtures thereof; and
   d) water, wherein:
      the latex formulation includes polyethylene oxide,
      the polyethylene oxide has a molecular weight ranging from 20 kDa to 1000 kDa,
      the latex formulation contains 0.2 to 1.0 phr (dry weight) of the polyethylene
      the latex formulation contains 0.15 to 0.45 phr (dry weight) of the polyethylene glycol or the derivative of polyethylene glycol, from the crosslinker, the latex formulation contains 0.005 to 0.075 phr (dry weight) of the metal-based compound from the crosslinker.

25. A latex formulation for preparing an accelerator-free nitrile rubber article comprising a mixture of at least one base polymer, a crosslinker, and a pH adjuster, wherein the crosslinker is an admixture of:
   a) metal-based compound, wherein the metal-based compound is a trivalent metal-based compound;
   b) polyethylene glycol or a derivative of polyethylene glycol, wherein the polyethylene glycol or derivative of polyethylene glycol has a molecular weight ranging from 200 Da to 20 000 Da;
   c) a hydroxide salt, wherein the hydroxide salt is selected from the group consisting of potassium hydroxide, sodium hydroxide, ammonium hydroxide and mixtures thereof; and
   d) water, wherein:
      the latex formulation includes polyethylene oxide,
      the polyethylene oxide has a molecular weight ranging from 600 kDa to 1000 kDa,
      the latex formulation contains 0.2 to 1.0 phr (dry weight) of the polyethylene oxide, and
      the latex formulation contains 0.05 to 0.45 phr (dry weight) of the polyethylene glycol or the derivative of polyethylene glycol, from the crosslinker.

* * * * *